United States Patent [19]

Cross et al.

[11] Patent Number: 4,627,838
[45] Date of Patent: Dec. 9, 1986

[54] STYLET ACTUATED WINGED CATHETER

[75] Inventors: David E. Cross, Tyne and Wear; Robert D. Adams, Bristol; Terence J. Floyd, Bath, all of England

[73] Assignee: Bard Limited, Sunderland, England

[21] Appl. No.: 679,947

[22] Filed: Dec. 10, 1984

[30] Foreign Application Priority Data

Dec. 9, 1983 [GB] United Kingdom ................. 8332983
Dec. 7, 1984 [GB] United Kingdom ................. 8430924

[51] Int. Cl.$^4$ ............................................. A61M 29/00
[52] U.S. Cl. ................................... 604/105; 604/164; 128/345
[58] Field of Search ................. 604/96, 104, 105, 106, 604/107, 115, 128, 164, 117, 166, 168, 170; 128/341, 345

[56] References Cited

U.S. PATENT DOCUMENTS

| 2,649,092 | 8/1953 | Wallace | 604/105 |
| 2,816,552 | 12/1957 | Hoffman | 128/341 |
| 3,344,791 | 10/1967 | Foderick | 604/104 |
| 3,490,457 | 1/1970 | Petersen | 604/105 |
| 3,713,447 | 1/1973 | Adair | 604/105 |
| 3,946,741 | 3/1976 | Adair | 604/164 |
| 4,069,826 | 1/1978 | Sessions et al. | 604/105 |
| 4,281,658 | 8/1981 | Child | 604/105 |

FOREIGN PATENT DOCUMENTS 0945861 4/1974 Canada ............................... 604/170

Primary Examiner—C. Fred Rosenbaum
Assistant Examiner—Jerome R. Smith, Jr.
Attorney, Agent, or Firm—Dennison, Meserole, Pollack & Scheiner

[57] ABSTRACT

In a catheter (10) with wings (26,27) which are brought into a retaining disposition by pulling on a distal tip insert (11) with an actuating means (16) manipulated from the proximal end of the catheter, the retaining surfaces (10B,31) move freely into their co-operative holding disposition from a transport disposition because they are spaced from one another in the transport disposition. The actuating means (16) is preferably a trocar and has a sleeve (19) which not only drives the catheter into position but also controls liquid flow down the catheter tube. Stop surfaces (29,10C) prevent "overshoot" of the wings past the desired retaining disposition and make more positive the disengagement of latching surfaces (22,23) between the tip element (11) and the trocar (16).

27 Claims, 4 Drawing Figures

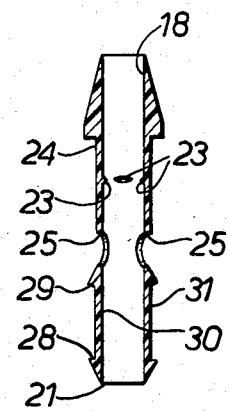
Fig.3.
Fig.4.

STYLET ACTUATED WINGED CATHETER

TECHNICAL FIELD AND INDUSTRIAL APPLICABILITY

This invention relates to a catheter. More particularly, but not exclusively, it concerns a suprapubic bladder catheter.

BACKGROUND ART

For many years there have been problems in achieving reliable temporary retention of the distal end of a catheter, by increasing the catheter tip section. A variety of solutions have been proposed and used. Perhaps the most common is to use a balloon. An example of such use can be found in a Foley bladder catheter. A balloon, however, has the disadvantages that it constitutes an undesirably large foreign body in the bladder, and that it requires an inflation channel in the wall of the catheter and an external means of inflating the catheter with a valve mechanism. This complicates the design of the catheter, reduces the maximum available lumen section for a given outside diameter and increases the external bulk of the catheter by the presence of an inflation funnel.

An alternative method of catheter retention uses a resiliently protruding formation which can be elastically deformed by an actuator to a non-protruding disposition for catheter insertion and removal. Examples are (i) "ears" formed from the catheter wall (Malecot catheters) or (ii) an increased diameter portion of the catheter tube at the tip thereof (De Pezzer).

These catheters suffer from a variety of problems. Firstly the "ears" may be so flexible that they do not give sufficient retention and may collapse if a slight pull is applied. The De Pezzer type of catheter tends not to give good retention as the diameter at the swollen tip of the catheter is limited. Additionally, it may be difficult to straighten out the swollen tip completely for insertion or removal.

Yet another method of catheter retention is to hold a tip formation in a protruding disposition by tension in an actuating rod or line which extends to the proximal end of the catheter. See British Patent Specification Nos. 688450, 955490, 1014570, 1046478 and 1463269 and U.S Pat. Nos. 1,828,986, 3,241,554, 3,261,357, 3,713,447 and 4,228,802. The catheters disclosed in these documents share the disadvantage of the balloon catheters, that the end of the catheter external to the patient (herein called the "outer" end) is cluttered by the presence of a tip erection means and that the lumen section available during use of the catheter is reduced by a connection between the tip and its erection means.

U.S Pat. No. 3,490,457 to Petersen discloses a catheter in which wings are brought into a projecting disposition by pulling on a tip insert tube with a thread which extends the length of the catheter tube to its proximal end. When the wings are erect the thread is removed.

Insertion of the catheter is effected by an obturator which is a stainless steel rod running the length of the catheter tube. The rod is of course removed after insertion and prior to use of the catheter.

The Petersen arrangement has a number of disadvantages. The thread arrangement is tricky to use. If the thread slips from the insert tube before the wings are erect the catheter must be discarded because the thread cannot be re-connected to complete the task. The insert tube is a tight sliding friction fit at all times in the catheter tube, so there is from beginning to end of the movement of the insert tube to erect the wings a considerable tension in the thread.

Further, there is possible substantially unimpeded flow of liquid along the catheter tube to the proximal end from the moment the distal end enters the bladder or other bodily fluid cavity. Such flow is inconvenient and could be unhygienic.

DISCLOSURE OF THE INVENTION

Amongst the objects of the present invention are the following: to provide a catheter which offers a surer and more reliable erection of a distal end retaining formation; to effect such erection in a movement which is impeded by frictional drag no more than necessary; to terminate positively the movement into the erect disposition so that the erect disposition of the retaining formation is predictable and constant and therefore always of maximum retentive effectiveness; to control fluid flow to the proximal end of the catheter so that it can be used as a signal of entry of the distal end of the catheter into the target bodily cavity and then terminates; and to provide a catheter which is economical to manufacture, not least by the use of as few component parts as possible.

According to a first aspect of the present invention there is provided a catheter comprising a patient (distal) end for location in a bodily cavity in a human or animal body, an outer (proximal) end to remain outside the vessel, a catheter tube which defines a fluid flow passage connecting the patient end and the outer end, a retaining formation at the patient end which formation is movable between a transport disposition wherein its diameter is substantially that of the flow passage and a retaining disposition wherein its diameter is sufficiently greater than that of the flow passage to prevent withdrawal of the patient end from the site, and actuating means which runs the length of the catheter tube and which is manipulated from the said outer end, in use of the catheter, for moving the retaining formation from the transport disposition into the retaining disposition, and which is thereafter removed from the catheter, characterised in that the retaining formation comprises: first and second holding surfaces which are spaced from one another in the transport disposition, which are brought towards each other in a closing movement, by the said manipulation of the actuating means, as the retaining formation moves into the retaining disposition, and which co-operate with each other at the retaining disposition to sustain the retaining formation in the retaining disposition.

According to a second aspect of the present invention there is provided a catheter which comprises: a catheter tube, having a hollow bore connecting a distal end which is for introduction into a bodily fluid cavity and a proximal end which is to remain outside the body; and an insertion rod for insertion in the bore and manipulation from the proximal end of the catheter to insert the distal end of the catheter in the bodily cavity: characterised in that the insertion rod has along its length a cross-section which is smaller than the internal cross-section of the catheter tube, so that liquid can flow between the rod and the tube, and an enlarged cross-section part at its distal end which forms a substantially liquid-tight seal with the catheter tube, and in that the tube has a through aperture in its wall which during insertion of the catheter into the cavity is just proximal of the enlarged cross-section part of the insertion rod, whereby arrival of the distal end of the catheter in the fluid cavity is signalled by a flow of fluid through the aperture and along the tube to the proximal end thereof, which flow is terminated by movement of the enlarged cross-section part to a position proximal of the aperture in the wall of the tube.

In the catheter of the invention, the co-operation of the holding surfaces is such as to assure reliable maintenance of the retaining formation in the retaining disposition, and their spacedness from one another helps to minimise frictional drag in their movement into the retaining disposition. Stop surfaces can be provided to prevent "overshoot" and ensure a predictable and constant relative position of the holding surfaces in the retaining disposition.

Preferably, the actuating means is a needle or trocar which also serves to drive the catheter tube into its inserted position in a bodily cavity. This arrangement reduces the number of component parts of the catheter. If the trocar shaft is spaced from the catheter tube but has a larger diameter portion at its tip there is the possibility of obtaining a fluid flow signal upon arrival of the catheter tip in the target bodily cavity which can be terminated by a relative movement of the trocar within the catheter tube.

It will be appreciated also that a catheter in accordance with the invention does not suffer in use from the above-mentioned disadvantages of restricted lumen section and outer end clutter.

In one embodiment, the end formation comprises a tip length of the flow passage and a tip element inserted in the tip length. The tip length is parted longitudinally in some way so that movement of the tip element towards the outer end widens the parted length.

In such an embodiment, establishment in the retaining disposition can be accomplished by providing a pair of holding surfaces which are brought together as the retaining formation moves to the retaining disposition to hold the formation in that disposition by frictional resistance between them. Preferably, a pair of latching surfaces is provided, one on the retaining formation and one on the actuator, which surfaces interact sufficiently positively to remain latched while the actuator is being used to bring into their frictional co-operation the pair of holding surfaces but otherwise permits removal of the actuator from the catheter after movement to the retaining disposition. A pair of releasing surfaces, one on the end formation and one on a release tool, which could, if desired, be the actuator, can be employed for releasing the pair of holding surfaces from their frictional co-operation to permit removal of the catheter from the body.

For a better understanding of the invention, reference will now be made, by way of example only, to one embodiment thereof, as shown in the accompanying drawings.

BRIEF DESCRIPTION OF THE DRAWINGS

FIG. 3 is a side elevation of the trocar and sleeve of the catheter; and

FIG. 4 is a longitudinal, diametral section of the tip moulding of the catheter.

BEST MODE FOR CARRYING OUT THE INVENTION

Figure 1:
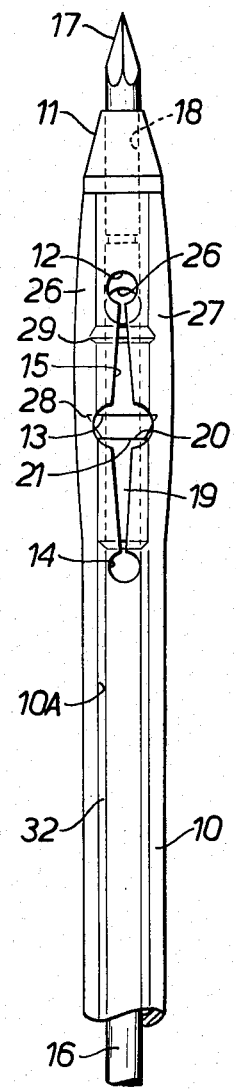
FIG. 1 is a side elevation of the patient end of the catheter, prior to insertion in the bladder of a patient.

Referring to FIG. 1, the catheter comprises a sufficient length of a suitable, synthetic polymeric catheter tube 10 which defines a fluid flow passage 10A. To the tube 10 is solvent bonded at the illustrated end thereof a moulded plastics tip element 11. The tip element 11 will be described in greater detail below with reference to FIG. 4. The leading end of the flow passage 10A, near the tip element 11, has in it a line of three through apertures 12,13, and 14 linked by a longitudinal slit 15. The apertures and slit extend through both the front and back wall of the passage 10, as seen in FIG. 1.

For insertion of the catheter, a needle 16, herein referred to as a trocar, but which constitutes also an actuator, extends the full length of the flow passage 10A from a grippable handle (not shown) which protrudes from the outer end of the flow passage 10A to a sharp point 17 which protrudes from a through bore 18 on the axis of the tip element 11. The diameter of the trocar 16 is smaller than the inside diameter of the catheter tube 10. A sleeve 19 bonded to the shaft of the trocar has an end surface 20 which butts against a similar end surface 21 of the tip element 11, and it is pressure between these two surfaces which carries the catheter into the bodily site as the trocar is pushed.

Referring now to FIGS. 3 and 4, it will be seen that the trocar 16 has an annular recess 22 a little way closer to the point 17 than the end surface 20. This recess 22 is intended to engage with a set of four protruding pips 23 on the bore 18 of the tip moulding 11. FIG. 4 also shows that the bore 18 is connected to the outer cylindrical surface 24 of the tip element (which has a diameter substantially the same as the interior diameter of the catheter tube 10) by a through aperture 25 which, as with the apertures 12,13 and 14 and the slit 15, extends through both the front and back wall of the element. The end surface 21 at the proximal end of the tip moulding 11 and an annular protrusion 29 are at opposite ends of an engagement sleeve 30 of the tip moulding, which has an external surface 31.

Figure 2:
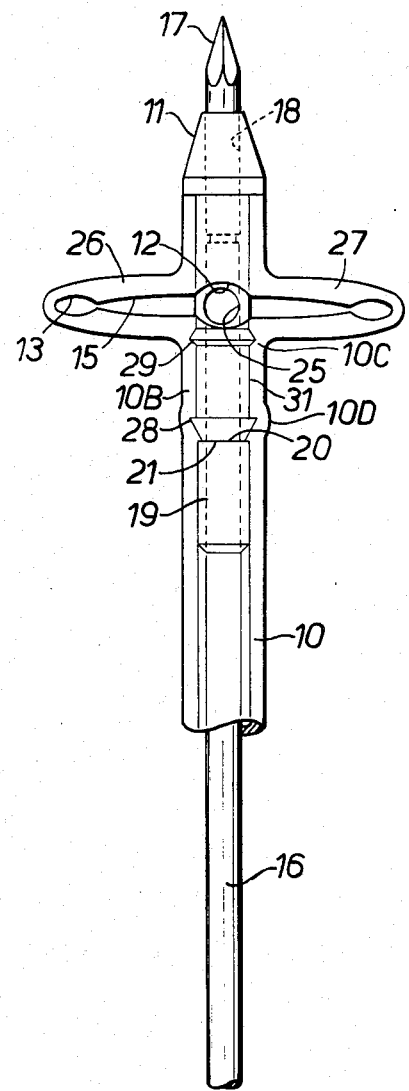
FIG. 2 is a similar elevation showing the retaining formation at the patient end having moved from the transport disposition to the retaining disposition.

Reverting to FIGS. 1 and 2, arrival of the catheter in the required disposition in the body e.g. in the bladder, will usually be indicated by flow of fluid, down the annular flow passage 32 between it and the shaft of the trocar 16, of fluid entering the passage through the end aperture 14. Such flow can be rapidly terminated simply by pulling the trocar 16 at its outer end, outwardly relative to the flow passage 10, to bring the outer end of the sleeve 19 into the unslit passage 10 below the aperture 14. The engagement between the pips 23 and the recess 22 is sufficiently positive to ensure that when such relative movement is initiated it is not these two surfaces which disengage but, rather, the lefthand 26 and righthand 27 side portions of the tip length of the flow passage 10 lying between the end apertures 12 and 14 which move apart from one another to widen the slit 15 and allow the distance between the end apertures 12 and 14 to be reduced.

Continued downward movement of the trocar 16 ultimately brings the end surface 21 of the tip element 11 to the region of the end aperture 14. As the engagement sleeve 30 of the tip element 11 (which constitutes one of a pair of holding surfaces) begins to enter the un-slit portion 10B of the flow passage 10 beneath the end aperture 14 (which portion 10B constitutes the other member of the pair), the annular protrusion 28 on the external end surface of the tip element 11 slightly stretches the material 10D of the flow passage 10, as the protrusion 28 moves down the bore thereof until it arrives at the stable position shown in FIG. 2. This stretching at 10D increases the grip of the catheter tube 10 on the engagement sleeve 30.

In this retaining position, the further annular protrusion 29 on the tip element 11 reaches the end 10C of the slit tip length of the flow passage 10 at the aperture 14. The protrusion 29 constitutes a first stop surface in that it is shaped and sized that the pressure required to drive it past the end or second stop surface 10C of the slit length of the catheter tube is greater than the disengagement force required to cause the pips 23 (which constitute one of a pair of latching surfaces) to depart from the recess 22 (which constitutes the other member of the pair of latching surfaces). Accordingly, at this point, as shown in FIG. 2, where the first stop surface 29 abuts the second stop surface 10C of the catheter tube adjacent the aperture 14, the connection between the trocar and the tip element 11 is reliably and reproducibly broken by the abutment of the surfaces 29 and 10C, and the trocar 16 may then be withdrawn from the flow passage 10, to leave the leading end of the catheter in its retaining disposition as shown.

The outside diameter of the sleeve 19 being a close fit within the flow passage 10, there is during this procedure no further passage of fluid to the outer end of the catheter after the sleeve 19 has entered the un-slit length of the passage. As the sleeve 19 approaches the outer end, it would be possible to nip or clip the flow passage 10 temporarily at some point in its length behind the sleeve 19 while the trocar is finally withdrawn and the outer end of the catheter connected to whatever fluid reception or delivery means is required. The arresting protrusion 29 is of course located such as to secure an orderly, predictable and repeatable configuration of the lefthand 26 and righthand 27 portions of the slit length of the flow passage 10, each neatly doubled back on itself. In the retaining disposition of the catheter, there is available for fluid flow not only the end bore 18 of the tip element 11 but also the side eyes 25.

It is to be particularly noted from FIG. 2 that the "wings" of the catheter are formed from relatively long and rigid strut elements 26 and 27 joined by short hinge elements 12,13 and 14. Wings of this nature are likely to be far more effective as retaining formations than are the analogous but more rounded protuberances of the prior art Malecot and De Pezzer proposals.

For removal of the catheter, all that is required is insertion in the flow passage 10 of a release tool having an end surface which is analogous to the end surface 20 of the trocar 16, such end surface serving to press the end surface 21 of the tip moulding so as to drive the annular protrusion 28 out of the un-slit length of the flow passage 10, upwardly past the end aperture 14. This release operation, by the end surface of the release tool and the end surface 21, permits thereafter the effects of natural relaxation of the material in the slit portions 26 and 27, and the effect of bodily tissue on the outer surface of the flow passage 10, to assist in bringing the slit portions 26 and 27 out of the doubled back configuration of FIG. 2 and into the transport disposition of FIG. 1, to permit complete withdrawal of the catheter from the body. The trocar 16 could be used as a release tool but otherwise it is preferable that the release tool does not protrude beyond the tip element 11.

The illustrated embodiment has a snap-fit connection (22,23) between the trocar and the catheter and a frictional compression fit (31,10B) between the holding surfaces in the retaining formation at the patient end of the catheter. It will be appreciated that, in other embodiments, it may be desirable to provide a snap-fit interengagement of portions of the retaining formation for increased certainty of its self-sustaining in the retaining disposition (for example, a stud and socket interengagement between the face-to-face lengths of each "arm" (26,27) of the "T" recognisable in FIG. 2) and, equally, the co-operation between the trocar and the catheter may be frictional instead of snap-fit.

In the illustrated embodiment the diameters of the outer surface 31 of the engagement sleeve 30 and the inside of the catheter tube 10 are such that the sleeve (without the protrusion 28) would not slide easily within the tube. In this way the whole of the surface 31 is a holding surface. If the relative diameters were changed, so as to allow easy relative sliding, the surface 31 would cease to perform a holding function and the holding function would be taken exclusively by the protrusion 28. In such an embodiment, the sleeve can extend into the unslit part 10B of the catheter tube 10, even in the transport disposition, provided that the protrusion 28 or other holding surface on the tip element does not.

It will also be appreciated that the presently preferred T-bar formation comprising arms formed from relatively short and flexible hinge elements (at the apertures 12,13,14 in the illustrated embodiment) will provide a more stable retaining configuration than a design such as that of prior Specification No. 688,450 where there are no portions of reduced rigidity to provide distinct hinge portions.

Those skilled in the art will be familiar with the considerations which surround choice of materials for use in catheters. In the present case, the materials must possess acceptable chemical inertness, resistance to hydrolytic degradation by both urine and water, non-toxic classification, sterilizability and susceptibility to viable manufacturing techniques. In addition, however, the co-operating components at the distal tip must possess the required degree of stiffness, elasticity and toughness as will ensure reliable performance of the holding and latching surfaces. The preferred method of fixing the tip element to the catheter tube is by solvent bonding so the chosen materials are preferably joinable in this way.

Those skilled in the art will recognise that suitable materials can be drawn from the polyurethanes, nylons (trade mark), polypropylenes, HD polyethylenes, polyacetate and polyvinylchloride. The presently preferred tip element materials are polyurethanes.

We claim:

1. A catheter comprising a patient (distal) end for location in a bodily cavity in a human or animal body, an outer (proximal) end to remain outside the body, a catheter tube which defines a fluid flow passage connecting the patient end and the outer end, a catheter retaining wind assembly immediately inward of the patient end which wing assembly is movable between a transport disposition wherein its diameter is substantially that of the flow passage and a retaining disposition wherein its diameter is sufficiently greater than that of the flow passage to prevent withdrawal of the patient end from the cavity, and actuating means removably received within and running the length of the catheter tube, said actuating means being manipulable from the said outer end for moving the retaining wing assembly from the transport disposition into the retaining disposition as said actuating means moves from said catheter tube through said outer end, and which is thereafter removed from the catheter, releasable latching means for releasably securing said actuating means to said catheter tube adjacent said patient end for movement of said patient end toward said outer end upon longitudinal retraction of said actuating means from said catheter tube through said outer end to effect said movement of said wing assembly into said retaining disposition, said latch means releasing upon predetermined increase in resistance to movement of said patient end, and means for providing said predetermined increase in resistance, said retaining wing assembly comprising first and second holding surfaces which interlock upon engagement, said first and second holding surfaces being spaced from one another in the transport disposition and engaging each other as the retaining wing assembly moves into the retaining disposition to sustain the retaining wing assembly on the retaining disposition.

2. A catheter as claimed in claim 1 wherein said means for providing said predetermined increase in resistance comprises first and second stop surfaces on said wing assembly, said first and second stop surfaces being spaced from one another in the transport disposition and abutting one another in the retaining disposition.

3. A catheter as claimed in claim 2 wherein the wing assembly includes a part of the length of the catheter tube which is divided longitudinally and defines opposed side portions which extend longitudinally of the catheter and face each other across a longitudinal plane of the catheter, said first holding surface being adjacent one end of the said side portions and the second holding surface being adjacent the other end of said side portions, said side portions outwardly bulging relative to each other on the bringing together of the holding surfaces to provide the necessary increase in diameter of the retaining formation.

4. A catheter as claimed in claim 3 wherein the side portions are defined by longitudinal slits in the said part of the length of the catheter tube.

5. A catheter as claimed in claim 4, including hinge means at the ends and middle of the side portions wherein the resistance of the side portions to bending stress is lower at the ends of the side portions and in the middle thereof than elsewhere along their length, so that the side portions bend preferentially at their ends and middle.

6. A catheter as claimed in claim 5 wherein the cross-section of each of the side portions is reduced at the ends of the side portions and in the middle thereof relative to the remainder of their length, the reduced cross-section defining the hinge means and providing the said lower resistance to bending.

7. A catheter as claimed in claim 6, wherein the reduced cross-section is established by an enlarged aperture at each end of each slit, and one midway along the length of each slit, the axis of each of the apertures lying within the plane of the slit in the catheter tube and parallel with the axis of the other two apertures.

8. A catheter as claimed in claim 3 wherein said wing assembly includes a tip element having a proximal end at which is said first holding surface, the second holding surface being located adjacent the proximal end of the said side portions of the catheter tube, said tip element being fixed to the patient end of the catheter and slidable within the catheter tube, said releasable latching means engaging between the tip element and the actuating means in such a way that applying to the actuating means a force which tends to pull it out of the proximal end of the catheter has the effect of sliding the first holding surface in the catheter tube into the said cooperation with the second holding surface.

9. A catheter as claimed in claim 8, wherein the second holding surface comprises an internal wall surface of the catheter tube, the first holding surface comprising an external surface of the tip element, said external surface defining an engagement sleeve, the holding surfaces providing a cooperation between the said holding surfaces which is a frictional telescopic engagement therebetween.

10. A catheter as claimed in claim 9, wherein the external surface of the engagement sleeve has an annular protrusion of an external diameter greater than the inside diameter of the catheter tube, so that the degree of said frictional engagement between the sleeve and the catheter tube is greatest over the surface of the protrusion.

11. A catheter as claimed in claim 9, wherein said stop surfaces comprise an annular protrusion on the external surface of the engagement sleeve and the catheter tube itself at the proximal end of the side portions, said stop surfaces limiting the length of telescopic overlap of the engagement sleeve within the catheter tube proximally of the longitudinally divided part of the tube.

12. A catheter as claimed in claim 8, wherein the tip element has a longitudinal through bore, and the actuating means is receivable in the bore, the bore serving to carry fluid, in use of the catheter, from the bodily cavity into the catheter tube.

13. A catheter as claimed in claim 12 wherein said latching means comprises at least one resilient protrusion on the bore of the tip element, and an annular recess in the actuating means received within the said bore.

14. A catheter as claimed in claim 8, wherein the tip element is plugged into the distal end of the cateter tube.

15. A catheter as claimed in claim 12, wherein the tip element has at least one transverse bore communicating with the said through bore and in use with the bodily cavity, at least when the holding portions are in the retaining disposition.

16. A catheter as claimed in claim 8, wherein the actuating means is an actuator rod which includes a shoulder thereon engageable against an annular surface of the tip element upon inward movement of the rod relative to the catheter tube to insert the catheter in the patient, the contact of the shoulder and annular surface transferrring the force via the tip element to the catheter tube.

17. A catheter as claimed in claim 1, wherein the actuating means is a trocar.

18. A catheter as claimed in claim 1, wherein the actuating means adjacent the distal end includes a larger diameter portion which forms a liquid-tight seal with the length of the catheter tube during withdrawl of the actuating means.

19. A catheter as claimed in claim 18 wherein the actuating means has a shaft which is of smaller diameter than the inside diameter of the catheter tube to permit liquid to flow into the annular space therebetween and out of the proximal end of the tube, the distal end of the catheter having liquid passages permitting liquid from the bodily cavity to flow into the annular space while the retaining formation is in the transport disposition to provide an indication of entry of the distal end of the catheter into the bodily cavity.

20. A catheter as claimed in claim 8, wherein the actuating means comprises a release tool having a shaft to extend up the catheter tube, and a shoulder to abut an annular surface of said tip element, movement of the holding surfaces back to the transport disposition being effected by applying to the proximal end of the shaft of the release tool and the catheter tube opposed forces of opposite direction calculated to urge the release tool relative to the catheter tube further towards the distal end of the catheter.

21. A catheter which comprises: a catheter tube, having a hollow bore connecting a distal end which is for introduction into a bodily fluid cavity and a proximal end which is to remain outside the body; and an insertion rod in the bore for manipulation from the proximal end of the catheter to insert the distal end of the catheter in the bodily cavity: wherein the insertion rod has along its length a cross-section which is smaller than the internal cross-section of the catheter tube, so that liquid can flow between the rod and the tube, and an enlarged cross-section part near its distal end which forms a substantially liquid-tight seal with the catheter tube, said tube having a through aperture in its wall just proximal of the enlarged cross-section part of the insertion rod, whereby arrival of the distal end of the catheter in the fluid cavity is signalled by a flow of fluid through the aperture and along the tube to the proximal end thereof, said rod with said enlarged cross-section part being longitudinally withdrawable through said proximal end with movement of the enlarged cross-section part to a position proximal of the aperture in the wall of the tube sealing said tube against flow until removal of said enlarged cross-section part through said proximal end.

22. A catheter as claimed in claim 1 wherein said actuating means comprises an insertion rod the insertion rod having along its length a cross-section which is smaller than the internal cross-section of the catheter tube, so that liquid can flow between the rod and the tube, and an enlarged cross-section part adjacent its distal end which forms a substantially liquid-tight seal with the catheter tube, said tube having a through aperture in its wall just proximal of the enlarged cross-section part of the insertion rod, whereby arrival of the distal end of the catheter in the fluid cavity is signalled by a flow of fluid through the aperture and along the tube to the proximal end thereof, said rod with said enlarged cross-section part being longitudinally withdrawable through said proximal end with movement of the enlarged cross-section part to a position proximal of the aperture in the wall of the tube sealing said tube against flow until removal of said enlarged cross-section part through said proximal end.

23. A catheter as claimed in claim 21 including catheter retaining wing assembly immediately inward of the distal end which wing assembly is movable between a transport disposition wherein its diameter is substantially that of the catheter tube and a retaining disposition wherein its diameter is sufficiently greater than that of the catheter tube to prevent withdrawal of the distal end from the cavity, and releasable latching means releasably securing said insertion rod to said catheter tube adjacent said distal end for movement of said distal end toward said outer end upon longitudinal retraction of said insertion rod from said catheter tube through said proximal end to effect said movement of said wing assembly into said retaining disposition, said latch means releasing upon predetermined increase in resistance to movement of said distal end, and means for providing said predetermined increase in resistance.

24. A catheter comprising a patient (distal) end for location in a bodily cavity in a human or animal body, an outer (proximal) end to remain outside the body, a catheter tube which defines a fluid flow passage connecting the patient end and the outer end, a wing assembly at the patient end, which assembly includes a tip element which has the form of a sleeve with a longitudinal bore therethrough, and an actuator rod which runs the length of the catheter tube and at its distal end is receivable within the sleeve, latch means detachably engaging the rod with the sleeve, the rod having a diameter less than the internal diameter of the catheter tube and being manipulable from the outer end of the catheter tube to carry the wing assembly from a transport disposition wherein the diameter of the assembly is substantially that of the flow passage to a retaining disposition wherein the diameter of the assembly is sufficiently greater than that of the flow passage to prevent withdrawal of the patient end from the cavity, said wing assembly including selectively interlocking first and second holding surfaces spaced from one another in the transport disposition and which are brought towards one another by the said manipulation of the rod to interlock with each other at the retaining disposition to sustain the wing assembly in the retaining disposition, such interlocking enabling detachment of the rod from the sleeve, and withdrawal of the distal end of the rod from the outer end of the catheter to leave the catheter tube unobstructed by the rod.

25. A catheter as claimed in claim 24, wherein the latch means comprises a recess on the rod and a resilient projection on the bore surface of the sleeve.

26. A catheter as claimed in claim 24, wherein the rod has near its distal end a portion of enlarged cross-section which is a liquid-tight fit in the catheter tube, said catheter tube having a liquid flow passage in its wall near its distal end for permitting liquid from the bodily cavity to flow into the tube proximally of the enlarged cross-section portion, said enlarged cross-section being selectively positioned distally beyond said liquid flow passage to allow flow through the proximal end of the tube, when the rod is fully inserted into the tube, said enlarged cross-section being selectively positioned proximally of said liquid flow passage to preclude flow through the proximal end of the tube as the rod is withdrawn from the tube, such withdrawal shutting off flow of liquid from the said flow passage to the outer end of the catheter tube until the enlarged portion emerges from the outer end of the catheter tube.

27. A catheter as claimed in claim 24, including a shoulder at the proximal end of the sleeve selectively abutted by the distal end of the enlarged portion to transmit from the rod to the catheter tube force for insertion of the catheter tube into the bodily cavity upon inward movement of the rod.

* * * * *